US012496056B2

(12) United States Patent
Mackool et al.

(10) Patent No.: US 12,496,056 B2
(45) Date of Patent: Dec. 16, 2025

(54) PUPIL EXPANDER

(71) Applicant: Richard Jonathan Mackool, Astoria, NY (US)

(72) Inventors: Richard Jonathan Mackool, Astoria, NY (US); Christopher Dean Smith, Ronkonkoma, NY (US); Luke Mackool, Astoria, NY (US)

(73) Assignee: Richard Mackool, Astoria, NY (US)

(*) Notice: Subject to any disclaimer, the term of this patent is extended or adjusted under 35 U.S.C. 154(b) by 730 days.

(21) Appl. No.: 17/844,811

(22) Filed: Jun. 21, 2022

(65) Prior Publication Data

US 2023/0404563 A1 Dec. 21, 2023

(51) Int. Cl.
*A61B 17/02* (2006.01)
*A61F 9/007* (2006.01)

(52) U.S. Cl.
CPC .......... *A61B 17/0231* (2013.01); *A61F 9/007* (2013.01)

(58) Field of Classification Search
CPC . A61B 17/0231; A61B 8/4209; A61B 8/4236; A61F 9/007; A61F 9/00736
See application file for complete search history.

(56) References Cited

U.S. PATENT DOCUMENTS 4,782,820 A * 11/1988 Woods ............... A61B 17/0231 600/236
5,267,533 A 12/1993 Smith
5,267,553 A * 12/1993 Graether ................. A61F 9/007 623/4.1
5,318,011 A * 6/1994 Federman .......... A61B 17/0231 606/107
5,322,054 A * 6/1994 Graether ............ A61B 17/0231 606/107
6,620,098 B1 9/2003 Milverton
6,648,819 B2 11/2003 Lee
8,323,296 B2 * 12/2012 Malyugin ........... A61F 9/00736 606/4

(Continued)

OTHER PUBLICATIONS

Tan et al., "Performance of a temperature-controlled shape-memory pupil expander for cataract surgery", Article in Journal of Cataract and Refractive Surgery, Jan. 2020, pp. 116-124, total of 10 pages.

(Continued)

*Primary Examiner* — Eduardo C Robert
*Assistant Examiner* — Steven J Cotroneo
(74) *Attorney, Agent, or Firm* — Collard & Roe, P.C.

(57) ABSTRACT

A pupil expander is formed from a frame of shape-memory material with a covering made of elastomer. The frame is in the form of two arc-shaped sections connected together at one end to form a broken circle having free distal ends. Each arc-shaped section has an upper frame portion and a lower frame portion connected to each other at the distal ends thereof. The covering is disposed over each arc-shaped section and has a C-shaped cross section so as to form an outwardly facing groove between the upper frame portion and the lower frame portion. The pupil expander is configured to be folded in half with the grooves facing each other and straightened so as to form a cylindrical body for insertion into a tubular applicator and upon release from the applicator, the pupil expander resumes the shape of the broken circle to push the margins of the pupil wider.

8 Claims, 8 Drawing Sheets

(56) References Cited

U.S. PATENT DOCUMENTS

| | | | | |
|---|---|---|---|---|
| 8,496,583 | B1 * | 7/2013 | Reynard | A61B 17/0231 600/235 |
| D756,515 | S | 5/2016 | Chin et al. | |
| D756,516 | S | 5/2016 | Chin et al. | |
| 9,339,375 | B2 | 5/2016 | Lee et al. | |
| 9,504,459 | B1 * | 11/2016 | Nallakrishnan | A61B 17/0231 |
| 9,763,653 | B2 | 9/2017 | Malyugin et al. | |
| 10,307,150 | B2 | 6/2019 | Kahook et al. | |
| 10,716,555 | B2 | 7/2020 | Girard et al. | |
| 11,172,916 | B2 | 11/2021 | Zacharia | |
| 11,219,438 | B2 | 1/2022 | Malyugin et al. | |
| 2003/0092970 | A1 * | 5/2003 | Lee | A61B 17/0231 600/236 |
| 2013/0131458 | A1 * | 5/2013 | Malyugin | A61B 17/0231 600/236 |
| 2013/0267988 | A1 * | 10/2013 | Sussman | A61B 17/0231 606/198 |
| 2014/0221759 | A1 | 8/2014 | Mackool et al. | |
| 2014/0276900 | A1 | 9/2014 | Cote et al. | |
| 2015/0164685 | A1 | 6/2015 | Bhattacharjee | |
| 2015/0366704 | A1 * | 12/2015 | Eippert | A61F 2/14 600/236 |
| 2016/0030239 | A1 * | 2/2016 | Akura | A61B 17/0231 606/107 |
| 2017/0265851 | A1 * | 9/2017 | Kahook | A61B 3/00 |
| 2018/0206835 | A1 | 7/2018 | Canabrava | |
| 2022/0071615 | A1 * | 3/2022 | Zacharia | A61B 17/0231 |

OTHER PUBLICATIONS

Stelzner, Sadiqa, "Pupil Expansion Devices and Mechanical Stretching of the Pupil", EyeWiki®, Oct. 5, 2021, total of 12 pages, Retrieved from: https://eyewiki.org/w/index.php?title=Pupil_Expansion_Devices_and_Mechanical_Stretching_of_the_Pupil&oldid=78960.

PCT Written Opinion of the International Searching Authority of International Application No. PCT/US 23/24781 (Aug. 4, 2003).

PCT—International Preliminary Report On Patentability Of International Application No. PCT/US2023/024781, Dated Dec. 18, 2024.

* cited by examiner

PUPIL EXPANDER

BACKGROUND OF THE INVENTION

1. Field of the Invention

This invention relates to a device for expanding the size of the pupil of the eye during cataract surgery, to enable better access to the lens by the surgeon. In particular, the invention relates to a pupil expander that can be attached to the edge of the iris directly from the applicator, without the need for extra positioning hooks or other devices.

2. The Prior Art

Cataract surgery involves removal and replacement of a patient's lens through the pupil of the eye. Pupil expanders are commonly used on patients with intraoperative floppy iris syndrome (IFIS) or other conditions which can interfere with pupil dilation. The pupil expander is inserted into the pupil and attaches to the edges of the iris and pulls the edges outward, to temporarily enlarge the pupil during surgery. The device is then removed after the cataract has been removed and the new lens inserted. These devices often take the form of folded and/or spring-loaded devices that are held in place via hooks or grooves on the edge of the iris. They are often placed into position using hooks or other positioning devices that place each section of the pupil expander into position. For example, the Malyugin ring, which is described in U.S. Pat. Nos. 8,323,296, 9,763,653, 11,219,438, is a flexible plastic ring having four sets of loops that that capture the edge of the iris to stretch it out. The ring is injected with an applicator and then placed into position with additional positioning devices.

In other devices, the pupil expander is injected directly onto the edge of the iris. For example, U.S. Pat. No. 5,267,553 to Graether discloses a flexible ring-shaped device that is folded and inserted into an injector. One folded end is then placed against the edge of the iris and the ring is then fed into the pupil to surround the edge of the iris. A placement hook can be used to position the ring. U.S. Pat. No. 6,648,819 to Lee discloses a ring having an open area so that the ring can be stretched out straight and placed in an injector in the straightened form. The ring is then fed into the pupil so that the end of the ring catches the edge of the iris and the rest of the ring follows around the circumference until the entire device is positioned on the edge of the iris. Other ring like devices are shown in U.S. Pat. No. 8,496,583 to Reynard and U.S. Pat. No. 4,782,820 to Woods.

While these devices show a variety of different structures and methods, they all suffer from significant drawbacks. Many of them require positioning hooks, which may overstretch the iris, causing damage. Other of the devices are made entirely of soft polymers, which do not have sufficient structural integrity to maintain a stable size and shape of the pupil during surgery. It would be desirable to provide a pupil expander that can be installed using only the injector, and which can maintain a stable shape and size during the entire procedure.

SUMMARY OF THE INVENTION

It is therefore an object of the invention to provide a pupil expander that is constructed of a stable, resilient material that can keep the iris at a defined shape and size during surgery, yet which can be applied to the edges of the iris using only the injector and no other positioning tools. This object is accomplished by a pupil expander comprising a frame formed of material having shape-memory characteristics, the frame being in the form of two arc-shaped sections connected together at one end to form a broken circle and having free distal ends, each arc-shaped section having an upper frame portion and a lower frame portion connected to each other at the distal ends thereof, and a covering over each arc-shaped section, the covering having a C-shaped cross section so as to form an outwardly facing groove between the upper frame portion and the lower frame portion. The pupil expander is configured to be folded in half with the grooves facing each other and straightened so as to form a cylindrical body for insertion into a tubular applicator, and whereupon upon release from the applicator, the pupil expander resumes the shape of the broken circle.

The frame can be formed of any suitable material, but is preferably formed of nitinol wire, which has superior shape memory characteristics and is lightweight. The covering is preferably formed of an elastomer, which has suitable elasticity and a smooth surface, so that application of the device to the iris minimizes friction between the device and the edges of the iris.

In one embodiment, the tips of the distal ends of the arc-shaped sections are bent inward toward an interior of the circle. This prevents any sharp or protruding portions from contacting the iris during application, as the point of first contact is the flat outer surface of the arc-shaped portions.

The frame can be formed in many different configurations, but is preferably constructed to a single piece of wire, with the connection between the two arc-shaped portions is formed by a curvature in the wire that extends toward an interior of the circle.

The invention also relates to method for applying the above-mentioned pupil expander into a pupil of a patient's eye, which involves the steps of folding the pupil expander so that the grooves face each other, feeding the folded pupil expander into a tubular injector with the distal ends of the pupil expander facing an exit end of the injector, injecting the folded pupil expander into a pupil of a patient such that the distal ends contact the edge of an iris of the patient as the pupil expander unfolds, and catch the edges of the iris in the grooves until the iris expander is fully inserted into the pupil with the grooves engaging the edge of the iris, and expanding the pupil by the pupil expander returning to the broken circle shape and pulling the edge of the iris outward after the step of injecting. Once the surgery is completed, the pupil expander can be removed using any suitable hooks or other tools to release the pupil expander from the edges of the iris. The pupil expander can be inserted into the pupil using a hook that is connected to the area of the frame between the arc-shaped portions, so that pushing the hook through the tubular injector forces the pupil expander of the injector into the pupil. The hook can also be used to help pull the pupil expander into the injector prior to use.

Once the pupil expander is fully in place on the edge of the iris, the hook can be disengaged from the iris expander leaving only the pupil expander in the eye. To remove the pupil expander, the hook can again engage the frame in the central uncovered region, and then pulled away from the pupil to peel the pupil expander away from the iris.

The device according to the invention has many advantages over the prior art, due to its unique combination of a shape memory frame covered by a soft elastomeric covering, as well as the unique shape, allowing it to be applied directly to the iris from the applicator without the need for any additional tools for placement after the device is injected into the eye. Use of the shape memory material allows the iris expander to gradually pull the edge of the iris into the expanded state after application of the device, thus minimizing damage to the iris.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
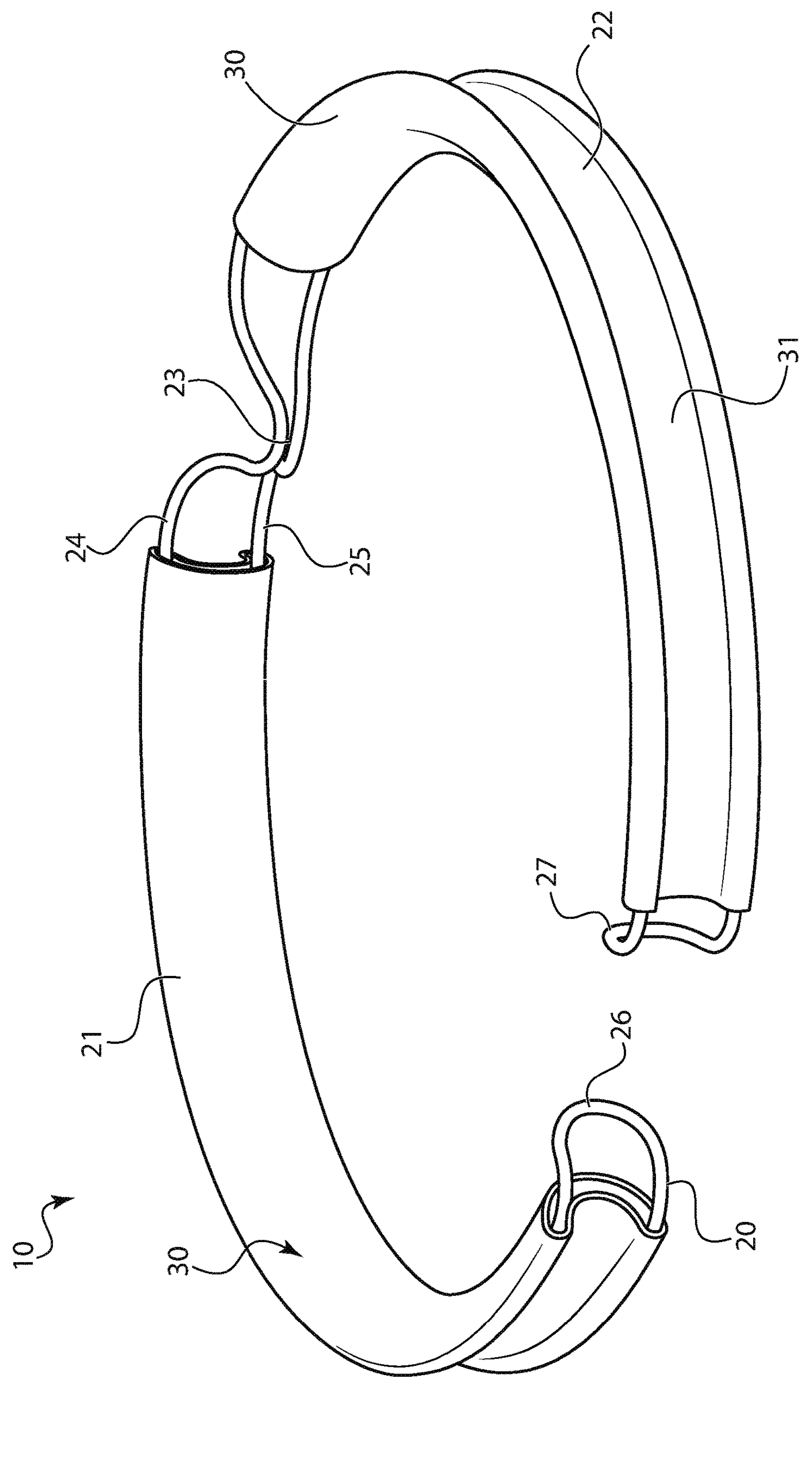
FIG. 1 shows a perspective view of the pupil expander according to the invention.
Figure 2:
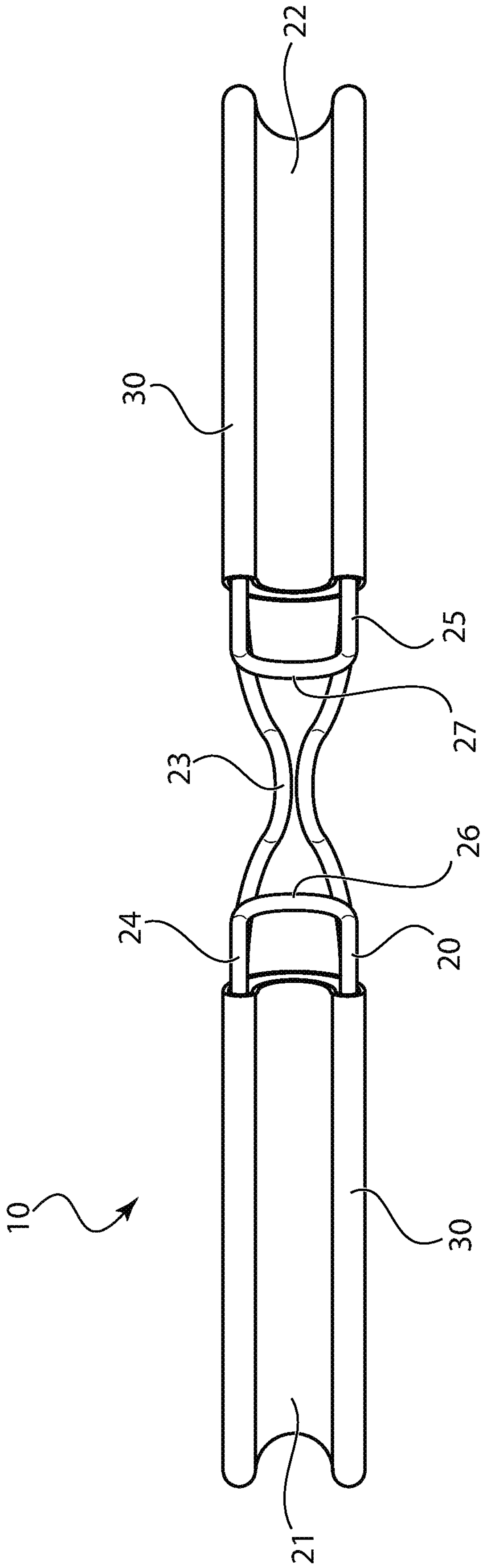
FIG. 2 shows a side view of the pupil expander.
Figure 3:
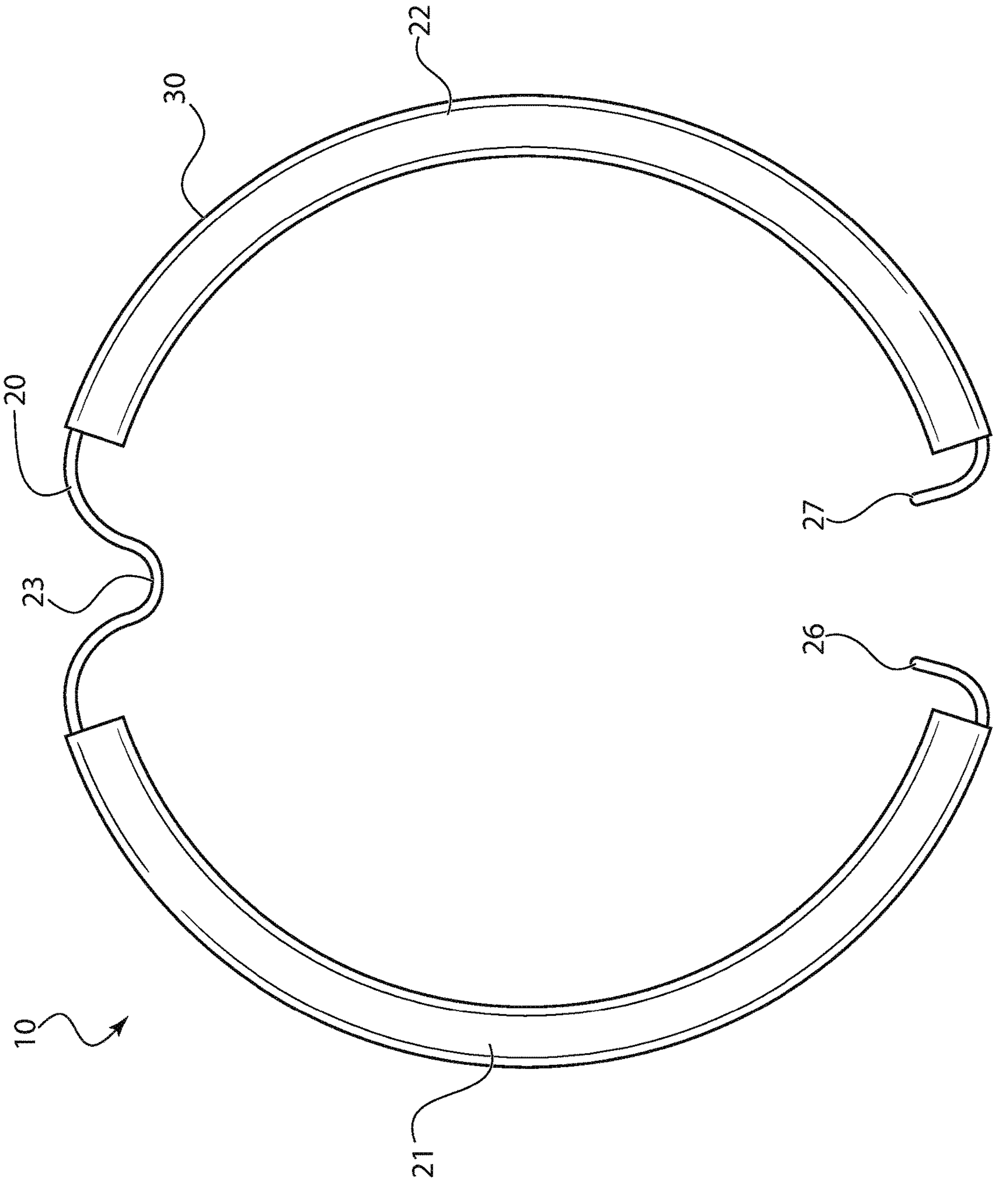
FIG. 3 shows a top view of the pupil expander.

Referring now in detail to the drawings and, in particular, FIGS. 1-4 show the iris expander 10 according to the invention, which is formed of a frame 20 surrounded by a covering 30.

The frame 20 is formed of a single piece of shape-memory material, such as nitinol wire, that is shaped so as to form two arc-shaped sections 21, 22, connected by a central indented portion 23 which faces toward an interior of a broken circle formed by the arc shaped sections 21, 22. Each of the sections of the frame are bounded by an upper frame portion 24 and a lower frame portion 25 that meet at distal ends 26, 27, so as to form the shape of the broken circle when viewed from above or below.

Each of the arc shaped sections 21,22 are covered by a covering 30 which between the upper frame portions 24 and lower frame portions 25 has a C-shaped cross section so as to form an outwardly facing groove 31 between the upper frame portion 24 and the lower frame portion 25. The covering 30 can be made of any suitable material, but is preferably a material that is soft, flexible and biocompatible, such as an elastomer. Specific materials could include natural rubbers, silicone elastomers, polyurethane elastomers, and nitrile rubbers, and fluoroelastomers, among others.

In one embodiment, the tips of distal ends 26, 27 of the of the arc-shaped sections of the frame 20 are bent inward toward an interior of the circle. This prevents the wire portions from contacting the edges of the iris during deployment, to create a smoother application of the pupil expander to the iris, as only the sections covered by the elastomer coating 30 are in contact with the iris.

Figure 4:
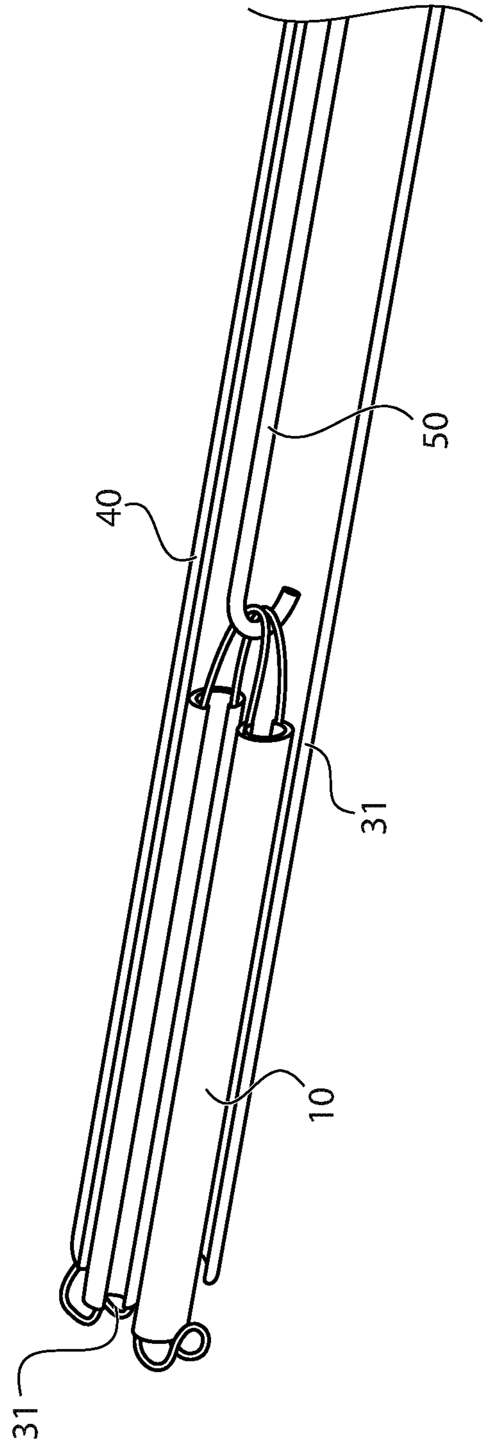
FIG. 4 shows a cut-away view of the pupil expander in a folded state inside a tubular injector.
Figure 5:
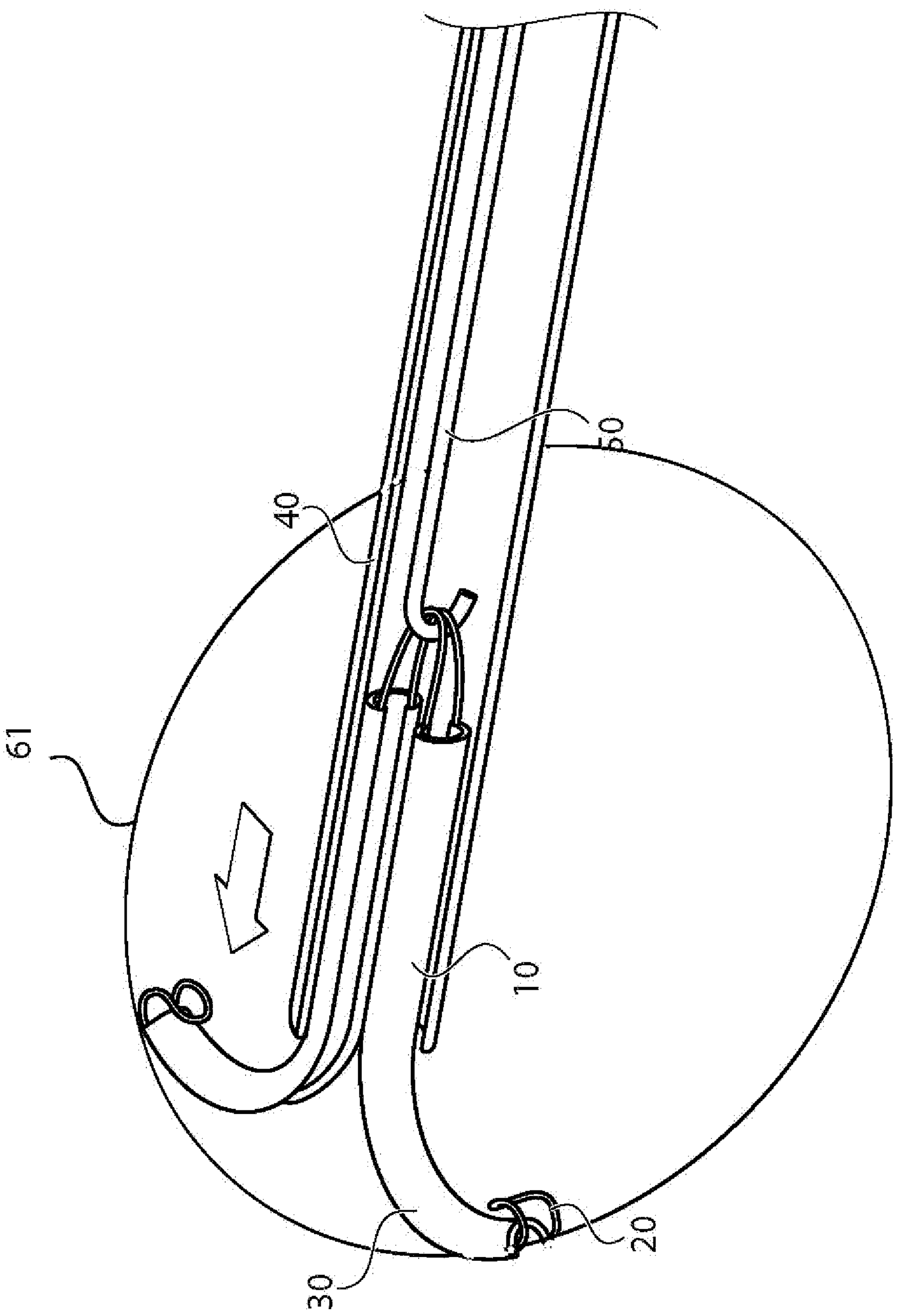
FIG. 5 shows a cut-away view of the pupil expander as it is being pushed out of the injector at about 33% deployment.
Figure 6:
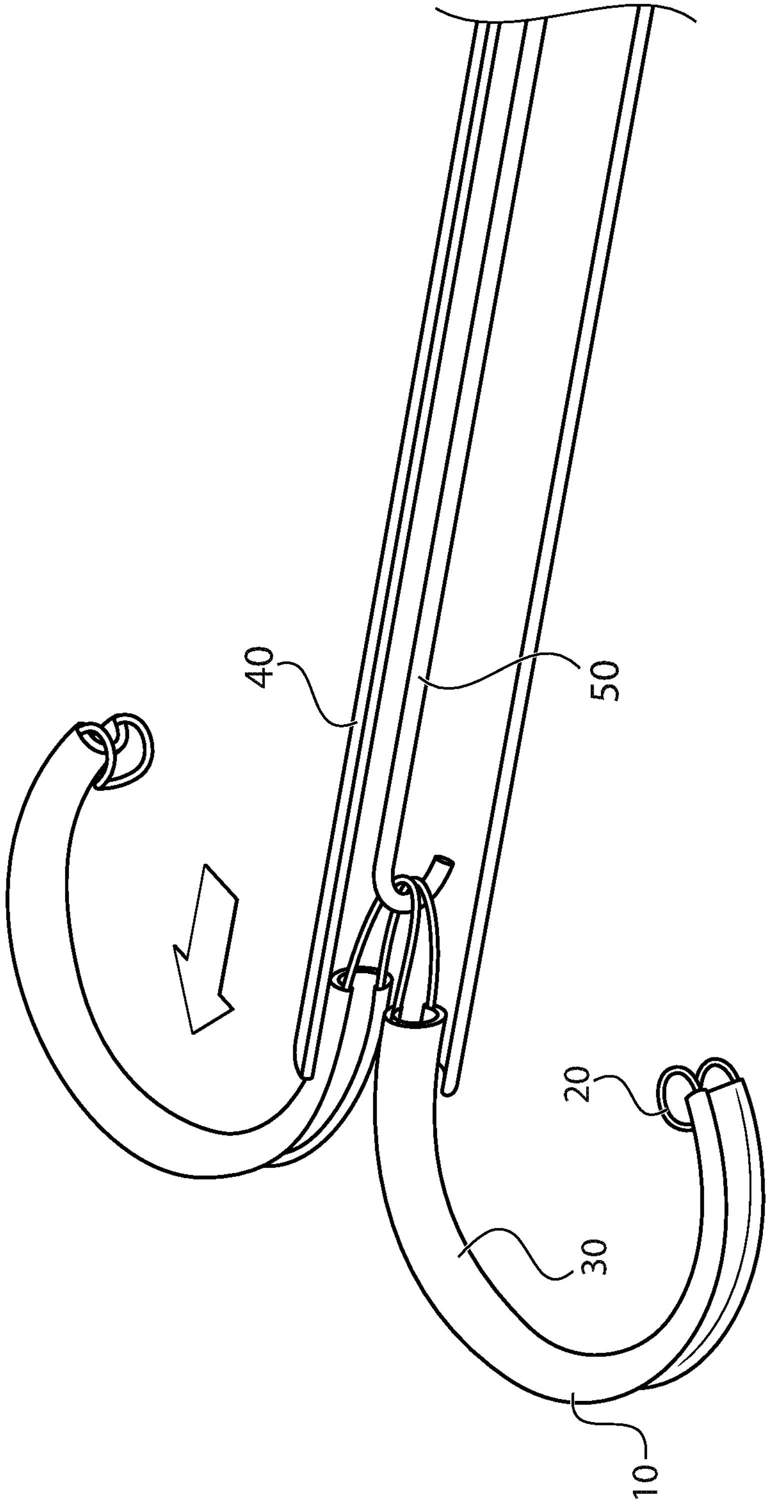
FIG. 6 shows a cut-away view of the pupil expander as it is about 66% deployed form the injector.
Figure 7:
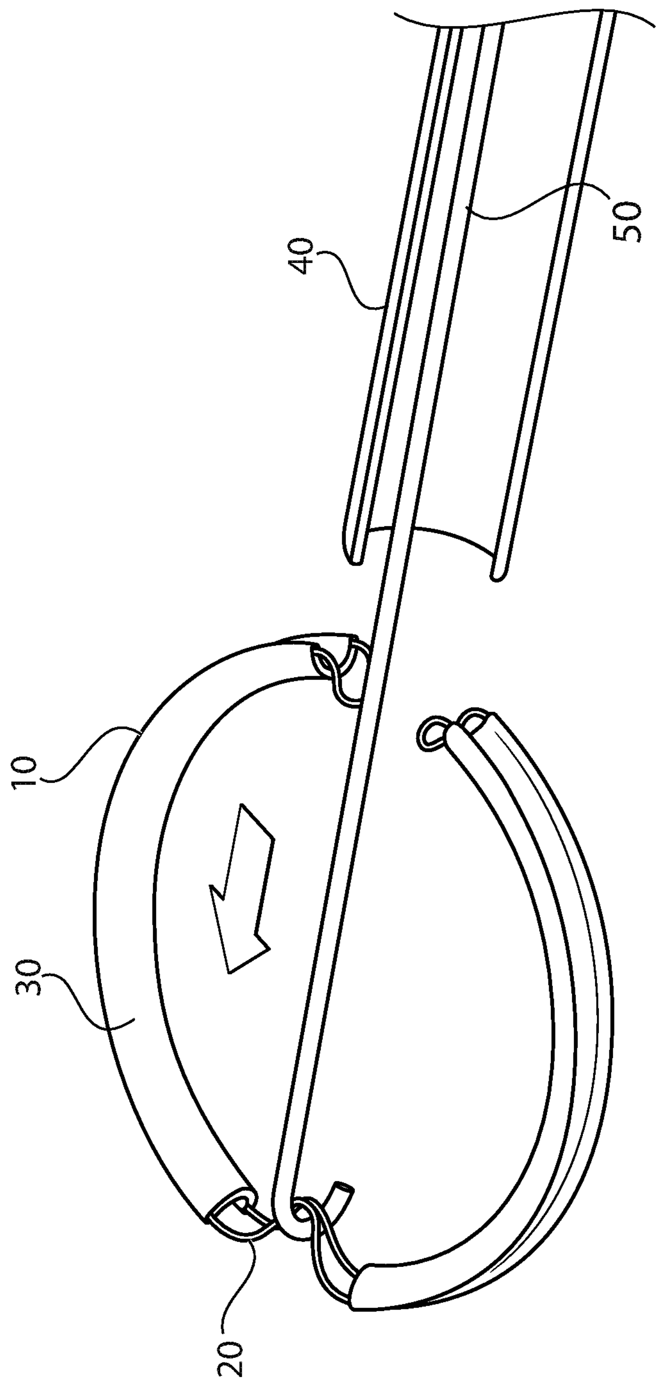
FIG. 7 shows the pupil expander fully removed from the injector with the hook still engaged.
Figure 8:
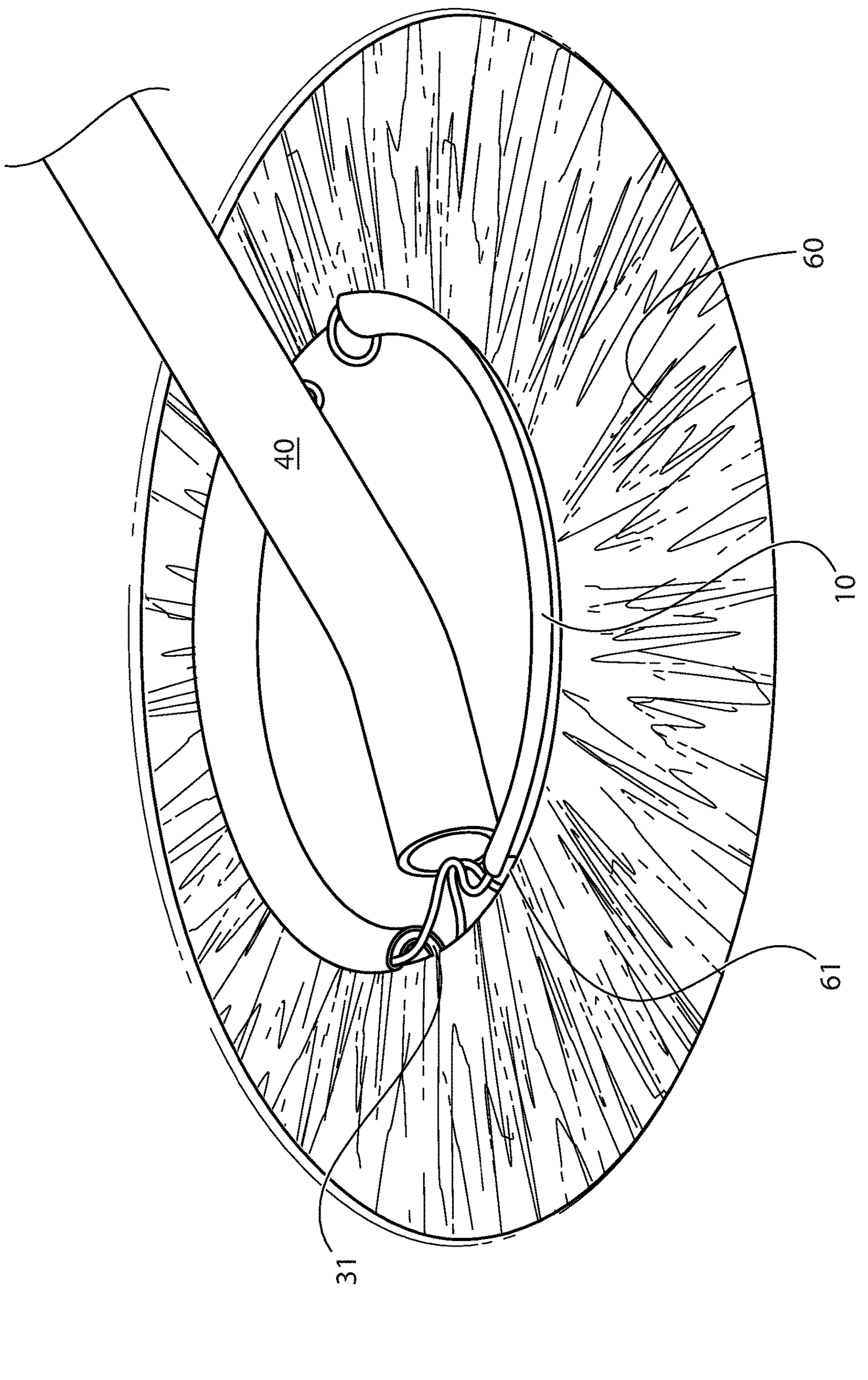
FIG. 8 shows the pupil expander in the fully deployed position on the edge of an iris of a patient.

The application of the pupil expander 10 to an iris 100 is described below with reference to FIGS. 4-8. As shown in FIG. 4, the pupil expander 10 is folded in half at the mid-point, so that the grooves 31 are facing each other and the outer surfaces of the arc-shaped sections 21, 22 form a tubular structure when straightened. The pupil expander 10 is fed into a tubular injector 40 and the central indented portion 23, which now extends proximally, is connected to a hook element 50 within the tubular injector 40. As shown in FIGS. 5-7, the pupil expander is then gradually pushed out of the tubular injector 40 by hook element 50, which lets the arc-shaped portions 21, 22 gradually return to their original curved shape, due to the shape memory material of the frame 20. During this process, the distal ends 26, 27 contact the edge 61 of iris 60 of a patient, and slide along the edge, catching the edge in grooves 31, until the entire pupil expander 10 has exited the tubular injector 40, as shown schematically in FIG. 5 and in FIG. 8. After full deployment, hook element 50 is removed from central portion 23, and the pupil expander is left to return to its fully circular shape, pressing the edge 61 of the iris 60 wider to enlarge the pupil for cataract surgery. When the surgery is finished, the pupil expander 10 can be removed by placing hook element 50 around central portion 23 of frame 20 and pulling pupil expander 10 away from the edge 61 of iris 60.

Accordingly, while only a few embodiments of the present invention have been shown and described, it is obvious that many changes and modifications may be made thereunto without departing from the spirit and scope of the invention.

What is claimed is:

1. A pupil expander comprising:

a frame formed of material having shape-memory characteristics, the frame being in the form of two arc-shaped sections connected together at proximal end to form a broken circle with free distal ends, each arc-shaped section having an upper frame portion and a lower frame portion, and a covering over each arc-shaped section, the covering having a C-shaped cross section so as to form an outwardly facing groove between the upper frame portion and the lower frame portion, wherein the pupil expander is configured to be folded in half with the grooves facing each other, and distal ends together, and straightened so as to form a cylindrical body for insertion into a tubular applicator, and whereupon upon release from the applicator, the distal ends move in opposite circumferential directions until the pupil expander resumes the shape of the broken circle.

2. The pupil expander according to claim 1, wherein the frame is formed of nitinol wire.

3. The pupil expander according to claim 2, wherein frame is constructed from a single piece of wire.

4. The pupil expander according to claim 3, wherein the connection between the two arc-shaped sections is formed by a curvature in the wire that extends toward an interior of the circle.

5. The pupil expander according to claim 1, wherein the covering is formed of an elastomer.

6. The pupil expander according to claim 1, wherein tips of the distal ends of the arc-shaped sections are bent inward toward an interior of the circle.

7. A method of inserting a pupil expander into a pupil of a patient's eye, wherein the pupil expander comprises a frame formed of material having shape-memory characteristics, the frame being in the form of two arc-shaped sections connected together at a proximal end to form a broken circle and having free distal ends, each arc-shaped section having an upper frame portion and a lower frame portion; and a covering over each arc-shaped section, the covering having a C-shaped cross section so as to form an outwardly facing groove between the upper frame portion and the lower frame portion on each arc-shaped portion, the method comprising:

folding the pupil expander so that the grooves face each other, feeding the folded pupil expander into a tubular injector with the distal ends of the pupil expander facing an exit end of the injector, injecting the folded pupil expander into a pupil of a patient such that the distal ends contact the edge of an iris of the patient as the pupil expander unfolds, and catch the edges of the iris in the grooves of the covering, with the distal ends sliding in opposite circumferential directions around the edge of the iris until the pupil expander is fully inserted into the pupil with the grooves engaging the edge of the iris, and expanding the pupil by the pupil expander returning to the broken circle shape and pulling the edge of the iris outward after the step of injecting.

8. The method according to claim 7, wherein the step of injecting comprises placing a hook around the frame between the arc-shaped portions and pushing the pupil expander out of the tubular injector by pushing the hook.

* * * * *